United States Patent [19]

Patel

[11] 4,268,361
[45] May 19, 1981

[54] INHIBITING POLYMERIZATION IN EXTRACTIVE DISTILLATION OF C-4 HYDROCARBONS USING ALKOXYNITRILE-CONTAINING SOLVENT

[75] Inventor: Pradeep V. Patel, Parma, Ohio

[73] Assignee: The B. F. Goodrich Company, Akron, Ohio

[21] Appl. No.: 150,848

[22] Filed: May 19, 1980

[51] Int. Cl.$^3$ .......................... B01D 3/40; C07C 7/08
[52] U.S. Cl. .......................................... 203/9; 203/35; 203/51; 203/53; 203/57; 203/58; 203/60; 203/65; 585/810; 585/833; 585/860; 585/864; 585/865; 585/950
[58] Field of Search .................... 203/9, 8, 35, 60, 57, 203/58, 65, 51, 53, 54; 585/950, 800, 807, 808, 810, 833, 837, 860, 864, 865

[56] References Cited

U.S. PATENT DOCUMENTS

| | | | |
|---|---|---|---|
| 3,329,582 | 7/1967 | Sennewald et al. | 203/8 |
| 3,462,484 | 8/1969 | Schnizer et al. | 203/8 |
| 3,515,762 | 2/1970 | Koide et al. | 203/9 |
| 3,551,507 | 12/1970 | Sakuragi et al. | 203/9 |
| 3,681,202 | 8/1972 | Funkhouser | 203/53 |
| 3,775,493 | 11/1973 | DeSimone et al. | 203/9 |
| 3,818,079 | 6/1974 | Sato et al. | 203/8 |
| 3,898,135 | 8/1975 | Tidwell et al. | 203/60 |
| 3,988,212 | 10/1976 | Watson | 203/9 |

*Primary Examiner*—Wilbur L. Bascomb, Jr.
*Attorney, Agent, or Firm*—J. Hughes Powell, Jr.; Ernest K. Bean

[57] ABSTRACT

Formation of butadiene-1,3 polymer during the extractive distillation of a C-4 hydrocarbon mixture to separate and purify butadiene-1,3 using a solvent composition in which an alkoxynitrile is present in a proportion of 50-99 percent by weight, is decreased through inclusion in the solvent of a synergistic combination of 2,4-dinitrophenol and phosphoric acid, each in a proportion of 0.05 to 0.5 percent by weight.

7 Claims, No Drawings

INHIBITING POLYMERIZATION IN EXTRACTIVE DISTILLATION OF C-4 HYDROCARBONS USING ALKOXYNITRILE-CONTAINING SOLVENT

BACKGROUND OF THE INVENTION

This invention relates to the separation and purification of C-4 hydrocarbons, particularly butadiene-1,3, from C-4 hydrocarbon mixtures utilizing extractive distillation with a selective solvent. It pertains to such extractive distillation when using a solvent composition containing as alkoxynitrile as an essential component and is specifically directed to modifying the solvent composition by including therein a combination of substances which function in a synergistic manner to prevent polymer formation during the extractive distillation operation.

It is well known to the art that C-4 hydrocarbon mixtures containing C-4 hydrocarbons of different degrees of unsaturation, such as mixtures of butadiene-1,3 with butanes (including n-butane and isobutane) and butylenes (including butene-1, and cis- and trans-butene-2) which are not easily separable by ordinary fractional distillation because of similarities in boiling points and azeotrope formation are much more efficiently separated into their individual components by the process of extractive distillation with a solvent of relatively higher boiling point which selectively dissolves the more-unsaturated butadiene-1,3 component. In the extractive distillation process as conventionally carried out, the selective solvent is introduced near the top of a distillation column and flows down the column as the distillation proceeds where it is contacted with the vapors of the hydrocarbons as they travel up the column. The more saturated hydrocarbons not dissolved by the solvent go overhead while the bottoms of the column contain the solvent plus the more unsaturated butadiene-1,3 component, which is removed from the solvent in a stripping column, or by other suitable means, and the lean solvent is recirculated to the column.

While a large number of selective solvents are known which can be used in the extractive distillation process, certain solvent compositions containing an alkoxynitrile are desirably used for the separation of butadiene-1,3 from C-4 hydrocarbon mixtures, because of their high degree of selectivity for butadiene-1,3 and their compatibility with existing plant configurations, provided the solvent composition preferably contains a substance, known as an inhibitor, which largely prevents the butadiene-1,3 in the solvent, necessarily exposed to elevated temperatures of the order of 80° to 160° C. or higher, from polymerizing to form polymer the presence of which results in fouling and plugging of equipment so that continuous operation over an extended period of time is difficult or impossible. The inhibitor should not itself polymerize or form an adduct with butadiene-1,3, as does furfural, and hence the known solvent compositions containing alkoxynitrile and furfural are not suitable.

My copending application Ser. No. filed concurrently herewith on, the disclosures of which are incorporated herein by reference, teaches means of modifying the known selective solvent compositions containing an alkoxynitrile to render them more suitable and, at the same time, to enable them to function in the extractive-distillation-purification of butadiene-1,3 without substantial formation of butadiene-1,3 polymer. It teaches, inter alia, that 2,4-dinitrophenol (DNP) is a unique inhibitor for butadiene-1,3 polymerization when present with an alkoxynitrile in a selective solvent composition.

SUMMARY OF THE INVENTION

It has been discovered that a combination of DNP and phosphoric acid ($H_3PO_4$) when present in alkoxynitrile containing selective solvent compositions for use in extractive distillation separation of butadiene-1,3 from C-4 hydrocarbon streams is a more effective inhibitor than DNP without phosphoric acid and that the two together exhibit a synergistic inhibiting action.

Accordingly, this invention provides a method for reducing the polymerization of butadiene-1,3 in a solvent composition containing an alkoxynitrile, such as 3-methoxy propionitrile (also known as beta-methoxy propionitrile) when exposed to elevated temperature, as in the process for extractive distillation separation of buradiene-1,3 from other C-4 hydrocarbons, which method consists of adding to the solvent, a small amount of a combination of DNP and phosphoric acid.

In another aspect the invention provides a novel solvent composition, for use in separating butadiene-1,3 from C-4 hydrocarbons of lesser degrees of unsaturation, particularly by extractive distillation, which solvent composition comprises an alkoxynitrile as an essential component to which is added small proportions, of the order of 0.05% to 0.5% of total composition, of each of DNP and phosphoric acid.

DETAILED DESCRIPTION OF INVENTION

In the practice of this invention a solvent composition as described below is used as the selective solvent for separation of butadiene-1,3 from C-4 hydrocarbon streams as described below by the extractive distillation process, operation of which is described below.

Solvent Composition.

There are three essential ingredients in the solvent composition of this invention. These are (1) an alkoxynitrile (2) DNP and (3) phosphoric acid. The alkoxynitrile is present in an amount from 40 to 99 percent by weight, the DNP in an amount from 0.05 to 0.5 percent by weight, preferably from 0.1 to 0.2 percent by weight and the phosphoric acid in an amount from 0.05 to 0.5 percent by weight, preferably from 0.1 to 0.2 percent by weight.

The alkoxynitrile component, as is well known from U.S. Pat. Nos. 3,436,437 and 3,895,138, is a compound of the formula $R_1$—O—$R_2$—CN wherein $R_1$ is an alkyl and $R_2$ is an alkylene radical each of which is preferably straight chain, but can also be branched chain, and contains from 1 to 3 carbon atoms. Specific alkoxynitriles are 3-methoxy propionitrile (MOP), which is most preferred, 3-ethoxy propionitrile (EOP), which is next preferred, 2-methoxy acetonitrile, 2-ethoxyacetonitrile, 3-methoxybutyronitrile, 4-methoxybutyronitrile, 4-propoxybutyronitrile, etc. and mixtures thereof. These alkoxynitriles are known from the above patents to dissolve butadiene-1,3 in preference to the less unsaturated butylenes and butanes.

In addition to the three essential components the solvent composition of this invention may contain other components which are cosolvents used with the alkoxynitrile. Water is a known cosolvent; it is preferably used with alkoxynitrile in solvent compositions not containing the essential DNP-phosphoric acid inhibitor combination of this invention and is also preferably present, in an amount from 1 to 20 percent by weight, in the solvent compositions of the invention. It is also desirable in many instances that one of the specific organic cosolvents disclosed in my copending application Serial No. filed as enhancing the selectivity of alkoxynitrile for butadiene-1,3 extractive distillation separation from other C-4 hydrocarbons—namely, dimethyl sulfoxide (DMSO), butyrolactone (BTL), N-methylpyrrolidone (NMP), sulfolane, morpholine, and trimethyl phosphate (TMP) be present in an amount from 5 to 20 percent by weight of the total composition. The presence of other cosolvents with the three essential components, or with the three essential components plus the preferred other components, is not excluded but does not result in further advantages and is not generally desirable.

C-4 Hydrocarbon Stream.

The C-4 hydrocarbon streams, subjected to extractive distillation in accordance with this invention, contain appreciable proportions, of the order of at least about 20 mole percent, of butadiene-1,3 and are derived from various sources as is well known to the art. One source is from the dehydrogenation or oxydehydrogenation of butanebutylene or butylene streams and another source is the by-product C-4 fraction from the pyrolysis of naphtha or other petroleum feedstocks under conditions to yield ethylene and/or propylene. In any event the C-4 hydrocarbon streams normally contain, in addition to butadiene-1,3, applicable proportions, as great or greater than the proportion of butadiene-1,3 of various butylenes including n-butene-1, trans-butene-2, cis-butene-2 and isobutylene as well as smaller proportions of butanes including n-butane and isobutane. Additionally other C-4 hydrocarbons such as butadiene-1,2 and acetylenic C-4 hydrocarbons such as butyne-2 and vinyl acetylene may be present, generally only in trace amounts, as may hydrocarbons lower or higher than C-4 such as propane, propylene and neopentane. When the C-4 stream is the effluent from oxydehydrogenation of butylenes it is also possible that non-hydrocarbon gases such as hydrogen, nitrogen, CO and $CO_2$ can be present. Any of the above or other C-4 hydrocarbon streams may be subjected to the extractive distillation process of this invention. Usually and preferably, however, the invention is applied to C-4 hydrocarbon streams containing from 20 to 90 mole percent butadiene-1,3, from 5 to 30 mole percent butene-1, from 1 to 5 mole percent trans-butene-2, from 1 to 15 mole percent cis-butene-2, from 1 to 20 mole percent isobutylene and from 1 to 15 mole percent butanes.

Operation of Extractive Distillation Process.

Processes for the extractive distillation of C-4 hydrocarbon streams are well known in the art and the operation thereof, considered apart from the selective solvent used therein, is not critical in this invention. The design and selection of equipment can be determined by those skilled in the art and the equipment present in existing commerical plants can be used in this invention without extensive modification. Conventional extractive distillation equipment may be used and may include baffle columns, bubble trays, packed columns etc. The number of theoretical plates and the length and diameter of the column will depend on the flow rates and the degree of extraction desired and can be calculated by known methods.

Generally the process is carried out by introducing the C-4 hydrocarbon stream into the column at a point near or below the mid-point of the column and introducing the selective solvent composition above the point of entrance of the C-4 hydrocarbon feed preferably at or above the top one-third of the column. Temperatures and pressure conditions are normally maintained such that the C-4 hydrocarbon feed is in the vapor phase. The vapor phase contacts the liquid phase countercurrently and the butadiene-1,3 vapors are preferentially extracted into the liquid phase. The vapors taken off overhead of the column thus contain a proportionately greater amount of the more saturated C-4 hydrocarbon components while the solvent composition containing proportionately more butadiene-1,3 is taken off at the bottom. The bottom stream is fed to a stripper where the solvent composition is freed from the dissolved more unsaturated hydrocarbons and recycled to the extractive distillation column. There can be various arrangements of equipment for separation of the overhead into components and for treatment of the bottoms of the column. For example, there may be side stream take offs, refluxes for part of the overhead, premixing of refluxes into the solvent, reboilers for the bottoms and removal of high boiling components from the solvent in a heavy ends column.

The temperature and pressure of the extractive distillation process will vary according to the particular C-4 hydrocarbon mixture being separated and the particular nature of the selective solvent composition but temperatures will generally be between 0° C. and 200° C. preferably in the range of 50° C. to 150° C., and pressures will range from atmospheric to 200 psig, but these are non-limiting pressure ranges since even sub-atmospheric pressures may in some instances be desirable.

The quantity of selective solvent composition will vary widely with the type of equipment and the desired efficiency of the separation but, in general, The quantity of solvent will range from 1 to about 15 parts by weight to 1 weight part of the C-4 hydrocarbon feed. The column may be operated with reflux and the reflux ratio may be varied widely.

Advantages from using the solvent composition of this invention, containing MOP or other alkoxynitrile and in which DNP and phosphoric acid are present, in the extractive distillation process as above described and the synergistic effect of the DNP phosphoric acid combination are shown in the following examples.

EXAMPLE 1

This Example is presented to illustrate the inhibition of butadiene-1,3 polymer formation when a combination of DNP and phosphoric acid is present in MOP solvent exposed to high temperature. It compares the amount of polymer formed when using each of DNP and phosphoric acid, without the other, with the amount formed when using the combination and thereby demonstrates the synergism resulting from the combination.

The following experimental technique is used to evaluate the effectiveness of DNP alone, phosphoric acid alone and a combination of the two in preventing butadiene-1,3 polymer formation when the butadiene-1,3 is dissolved in MOP, as in an extractive distillation process, and held at elevated temperatures. The MOP solvent is first distilled in the presence of caustic soda to remove acidic impurities which may be present and is then analyzed for acid and alkali both of which are absent from the distilled MOP solvent.

In each of four runs 400 grams of the distilled MOP, with and without DNP and/or phosphoric acid added thereto, as will be shown as inhibitors for the four runs, are then charged to a carbon steel cylinder. Twenty-five grams of carbon steel chips are added to provide additional surface area for fouling. The cylinder is purged with nitrogen, evacuated and liquid butadiene-1,3 (which has been distilled under nitrogen to remove impurities such as butadiene dimer which may have been present) is injected into the cylinder. The cylinder is weighed and it is determined that 60 grams of butadiene-1,3 are added. The cylinder is then placed in an oil bath maintained at 295° F. for 48 hours. The cylinder is removed from the oil bath, cooled, and reweighed whereby it is determined that no butadiene-1,3 is lost. Its contents are then filtered. The material remaining on the filter paper is dried in a vacuum oven and weighed. This is a portion of the insoluble polymer, called (A). The filtered solvent-butadiene-1,3 mixture is distilled under vacuum and the material remaining in the pot is coagulated with methanol, washed and dried in a vacuum oven and weighed. This is the soluble polymer called (B). The carbon steel cylinder is then filled with toluene and held in an oil bath for 48 hours at 295° F. whereby polymer sticking to the sides of the cylinder and to the chips is dissolved in toluene. After distilling off the toluene under vacuum the residual polymer is coagulated with methanol, filtered, washed, dried, and weighed. This material is called (C), plus (A) is the insoluble polymer and (B) is the soluble polymer. Thus total polymer formation is the sum of (A), (B), and (C). The polymer formed is expressed as a percentage of the initial content of butadiene-1,3 (BD).

The following table shows the amount of DNP and $H_3PO_4$ used in each of the four runs and the amount of polymer formed.

| Run No. | Inhibitor Additive | Concentration of Inhibitor Additive (ppm) | % Total Polymer Based on BD Content (A + B + C) |
|---|---|---|---|
| 1 | None | 0 | 5.17 |
| 2 | DNP | 1,000 | 3.01 |
| 3 | $H_3PO_4$ | 1,700 | 5.25 |
| 4 | Combination of DNP | 1,000 | |
| | $H_3PO_4$ | 1,700 | 1.24 |

It is apparent from the table that $H_3PO_4$ alone does not inhibit butadiene-1,3 polymerization, but that its presence in combination with DNP (which does inhibit butadiene-1,3 polymerization) remarkably and unexpectedly improves the effectiveness of the DNP in a synergistic fashion.

Because MOP may decompose at the temperature of the test to produce acrylonitrile which is a polymerizable material which could also lead to polymer formation, the technique described above is repeated except that no butadiene-1,3 is added to the MOP solvent in order to determine the extent of MOP decomposition and subsequent polymerization of acrylonitrile. When no inhibitor, or DNP inhibitor without $H_3PO_4$ in a concentration of 1,000 ppm is used in the MOP, the percent polymer based on 60 grams is 0.68 percent indicating that a portion of the total polymer in those cases could have resulted from acrylonitrile polymerization and that DNP did not inhibit this polymerization. When $H_3PO_4$ is used without DNP in the same 1,700 ppm concentration the percent polymer on the same basis is 0.32 percent indicating an expected 0.36 percent (0.68-0.32) reduction in the total amount of polymer when using 1,000 ppm DNP and also using 1,700 ppm phosphoric acid. Thus in the presence of BD the polymer formed in Run 3 above is expected to be reduced by 0.36 percent to an expected total of 2.65 percent polymer from the 1,000 ppm DNP+1,700 ppm phosphoric acid combination. The fact that in actuality the total polymer formation from 1,000 ppm DNP combined with 1,700 ppm phosphoric acid was much less—i.e. 1.24 percent—establishes the synergistic result obtained from the combination.

The experimental technique described in this example can also be employed to demonstrate a synergism in the polymerization inhibiting effect of 0.05 to 0.5 weight percent (500 to 5,000 ppm) of DNP combined with 0.05 to 0.5 weight percent (500 to 5,000 ppm) of $H_3PO_4$ when present in MOP solvent, or aqueous MOP solvent containing 1 to 20 percent weight percent water and/or 5 to 30 weight percent organic cosolvent such as DMSO, BTL, NMP, sulfolane, morpholine or TMP.

EXAMPLE 2

This Example is presented to describe the separation of butadiene-1,3 from a C-4 hydrocarbon stream by the extractive distillation process using MOP solvent containing a combination of DNP and $H_3PO_4$.

A two-inch diameter stainless steel extraction distillation column with 95 seive trays and a tray spacing of 1.875 inches is used to separate a mixture of C-4 hydrocarbon containing about 43% butadiene-1,3, 20% butene-1, 4% cis-butene-2, 6% trans-butene-2, 24% isobutene, 2% n-butane, 1% isobutane and 0.1% vinyl acetylene and methyl acetylene. This C-4 hydrocarbon feed is introduced into the column below its mid-point on tray no. 35 (counting from the bottom) at a rate of 5 to 8 grams per minute. An extractive distillation solvent composition containing in one run 95% MOP and 5% water and in another run 75% MOP, 20% DMSO, and 5% water, each containing 1,500 ppm DNP and 1,000 ppm $H_3PO_4$, is introduced into the column at a point near the top of the column on tray no. 90 (from the bottom) at a rate of 35 to 40 grams per minute, the ratio (wt/wt) of solvent to hydrocarbon feed thus being from 5 to 8.

The top of the column is maintained at a temperature of about 130° F. and a pressure of about 80 psia while the bottom of the column is maintained at a temperature of about 230°-240° F. and a pressure of about 80 psia. During operation of the column, separation of butadiene-1,3 from the other C-4 hydrocarbons occurs as a distilled stream much leaner in butadiene-1,3 than the feed is taken overhead (with a reflux stream returned) and a liquid stream from the bottom of the column rich in butadiene-1,3 is passed through a stripping column where the butadiene-1,3 is separated by distillation and the lean solvent recycled to the column.

The column is operated in each run continuously for a period of over 500 hours but there is no indication whatsoever of polymer formation, either butadiene-1,3 polymer or acrylonitrile polymer, at any point in the system and operation proceeds without difficulties due to fouling or plugging of equipment thus demonstrating the effectiveness of the DNP plus $H_3PO_4$ inhibitor combination under actual operating conditions.

I claim:

1. A method of reducing the tendency of butadiene-1,3 to polymerize in a solvent composition comprising from 50 to 99 percent by weight of an alkoxynitrile of the formula $R_1$—O—$R_2$—CN wherein $R_1$ is alkyl and $R_2$ is alkylene each containing from 1 to 3 carbon atoms, when exposed to elevated temperature, which comprises including in the solvent composition from 0.05 to 0.5 percent by weight of 2,4-dinitrophenol and 0.05 to 0.5 percent by weight of phosphoric acid.

2. The method of claim 1 wherein the alkoxynitrile is 3-methoxy propionitrile.

3. The method of claim 2 wherein the solvent composition also contains from 1 to 20 percent by weight of water.

4. In an extractive distillation process for separating butadiene-1,3 from a C-4 hydrocarbon stream containing C-4 hydrocarbons more saturated than butadiene-1,3 which process includes the steps of (a) introducing a selective solvent to an extractive distillation column (b) introducing said C-4 hydrocarbon stream to said column at a point below the point of introduction of said selective solvent (c) selectively extracting butadiene-1,3 from said C-4 hydrocarbon stream to form a liquid solvent fraction richer in butadiene-1,3 (d) withdrawing overhead from said column a vaporous C-4 hydrocarbon fraction richer in hydrocarbons less saturated than butadiene-1,3 (e) withdrawing said liquid solvent fraction richer in butadiene-1,3 from the bottom of said column (f) introducing said withdrawn liquid solvent fraction to a stripping column to remove said butadiene-1,3 and (g) recycling the lean solvent to said extractive distillation column, and in which process the selective solvent contains from 50 to 90 weight percent of an alkoxynitrile of the structure $R_1$—O—$R_2$—CN wherein $R_1$ is an alkyl and $R_2$ is an alkylene group each containing from 1 to 3 carbon atoms, the improvement which consists of including in the selective solvent composition a combination of 0.05 to 0.5 percent by weight of 2,4 dinitrophenol and 0.05 to 0.5 percent by weight of phosphoric acid.

5. The process improvement of claim 4 wherein the alkoxynitrile is 3-methoxy propionitrile.

6. The process improvement of claim 5 wherein there is included in the selective solvent composition from 0.01 to 0.2 percent by weight 2,4 dinitrophenol and 0.01 to 0.2 percent by weight of phosphoric acid.

7. The process improvement of claim 6 wherein there is additionally included in the selective solvent composition from 1 to 25 percent by weight of water and from 5 to 30 percent by weight of an organic cosolvent selected from the class consisting of dimethyl sulfoxide, sulfolane, butyrolactone, N-methyl pyrrolidone, morpholine, and trimethyl phosphate.

* * * * *